(12) United States Patent
Haut et al.

(10) Patent No.: US 7,320,701 B2
(45) Date of Patent: Jan. 22, 2008

(54) PUSH-IN SUTURE ANCHOR, INSERTION TOOL, AND METHOD FOR INSERTING A PUSH-IN SUTURE ANCHOR

(75) Inventors: Traci Haut, Okemos, MI (US); Michael Francis Keane, North Wales, PA (US); Mark Paiste, Springfield, PA (US); William Reimels, West Chester, PA (US)

(73) Assignee: Linvatec Corporation, Largo, FL (US)

( * ) Notice: Subject to any disclaimer, the term of this patent is extended or adjusted under 35 U.S.C. 154(b) by 658 days.

(21) Appl. No.: 10/453,444

(22) Filed: Jun. 2, 2003

(65) Prior Publication Data

US 2004/0243178 A1    Dec. 2, 2004

(51) Int. Cl.
*A61B 17/04* (2006.01)
(52) U.S. Cl. .................................. 606/232; 606/72
(58) Field of Classification Search ............. 606/232, 606/72
See application file for complete search history.

(56) References Cited

U.S. PATENT DOCUMENTS

| | | | |
|---|---|---|---|
| 4,968,317 A | 11/1990 | Törmälä | 606/77 |
| 5,405,359 A | 4/1995 | Pierce | 606/232 |
| 5,522,845 A | 6/1996 | Wenstrom, Jr. | 606/232 |
| 5,527,342 A * | 6/1996 | Pietrzak et al. | 606/232 |
| 6,045,573 A * | 4/2000 | Wenstrom et al. | 606/232 |
| 6,440,154 B2 * | 8/2002 | Gellman et al. | 606/232 |
| 6,610,080 B2 * | 8/2003 | Morgan | 606/232 |
| 6,887,259 B2 * | 5/2005 | Lizardi | 606/232 |
| 6,939,355 B1 * | 9/2005 | Gellman et al. | 606/144 |
| 6,986,781 B2 * | 1/2006 | Smith | 606/232 |
| 2003/0181946 A1 * | 9/2003 | Bartlett | 606/232 |

FOREIGN PATENT DOCUMENTS

| | | |
|---|---|---|
| FR | 2 750 031 | 12/1997 |
| WO | WO 01/06933 | 2/2001 |

\* cited by examiner

*Primary Examiner*—Michael J. Hayes
*Assistant Examiner*—Michael G. Mendoza
(74) *Attorney, Agent, or Firm*—Ostrolenk, Faber, Gerb & Soffen, LLP

(57) ABSTRACT

A toggling suture anchor, insertion tool, and method for anchoring at least one suture thread to a bone are provided. The toggling suture anchor is anchored by operation of the insertion tool, the suture anchor including a shaft having a longitudinal axis, a distal end, a proximal end, at least one eyelet hole to receive the suture thread, and at least one suture groove to provide a location to guide the suture thread while inserting the suture anchor into the bone; and at least one locking wing extending radially from the shaft, the locking wing being provided on one side of a first plane, the first plane including the longitudinal axis of the suture anchor.

26 Claims, 21 Drawing Sheets

PUSH-IN SUTURE ANCHOR, INSERTION TOOL, AND METHOD FOR INSERTING A PUSH-IN SUTURE ANCHOR

FIELD OF THE INVENTION

The present invention relates to a surgical implant for attachment of soft tissue to bone, an insertion tool for anchoring suture anchors to bone, and a method for anchoring a suture anchor to bone.

BACKGROUND OF THE INVENTION

It is often necessary to attach soft tissue to bone, for example, to attach ligament tissue to bone tissue. Loss of integrity in bone tissue, for example, a ligament of a human rotator cuff, as well as recurrent dislocation of the shoulder, may result in abnormal kinematics of the shoulder. This may cause progressive weakness of the shoulder and, in some circumstances, severe dysfunction of the shoulder and progressive degenerative joint changes. Accordingly, procedures have been developed to repair, for example, the rotator cuff, to prevent debilitating loss of function and to restore more physiologic biomechanics. However, these conventional procedures may require invasive surgical procedures, which may lead to increased complications and increased morbidity.

In response, various minimally invasive techniques for reattaching tissue to bone have been developed, such as the techniques referred to in Gartsman, G. M. et. al., "Arthroscopic Repair of Full Thickness Tears of the Rotator Cuff", J Bone Joint Surg Am 1998; 80:832-840. Many of these techniques describe the use of suture anchors to maintain proximity between soft tissue and bone, thereby facilitating re-attachment of the soft tissue to the bone.

Many of the early suture anchors were operable to be screwed into the bone. However, to properly secure such an anchor, the bone had to be first prepared by a separate tapping step (i.e., a pre-drilling step). In an effort to eliminate the initial tapping step, push-in type anchors were developed. The effectiveness of push-in type anchors may be measured by their ability to reliably set in all bone types, the size of the anchor, and the effectiveness of insertion tools for protecting suture threads while inserting the anchors into bone.

With respect to push-in type suture anchors, the insertion tool, the suture implant, and the method of insertion should act to consistently and reliably set the implant in a variety of bone types. For this purpose, the implant should be designed as small as possible to limit the amount of foreign substance in the body, and should have features configured to consistently set the anchor into bone.

U.S. Pat. No. 5,618,314 to Harwin et al. relates to an anchor with a plurality of wing members fixed distally on the proximal end thereof. As characterized, the wing members are symmetric about the longitudinal axis of the anchor, and configured to be inserted straight into bone. After insertion into bone, the wing members expand outwardly to cause fixation of the anchor to the bone. However, it is believed that such a design may not provide sufficient fixation in soft bone.

U.S. Pat. No. 5,690,676 to Dipoto et al. relates to an anchor having one or more fixed rib members symmetrically arranged around a longitudinal axis of the anchor. As characterized, the anchor is driven into bone by an external force applied to the proximal end of the anchor (i.e., the back of the anchor). Effective insertion of the anchor into the bone requires that the anchor be driven on a 'straight-line' trajectory, without a second fixation step (e.g., a rotation step) for positive engagement of the ribs to the bone. In this manner, the anchor requires the elastic action of good bone to spring back into place after passage of the fixed rib members to prevent the anchor from exiting the bone once inserted. However, in soft or poor quality bone, bone elasticity may be negatively affected, which may cause inadequate fixation of the anchor to the bone.

U.S. Pat. No. 5,527,342 to Pietrzak et al. relates to a suture anchor having a rib for fixation to bone. In one embodiment, the rib extends radially from the longitudinal axis to the bone, but is not intended to be toggled into a final locked position. In this manner, it is believed that such a configuration does not effectively fix within bone.

U.S. Pat. Nos. 6,146,407 and 6,165,203 to Krebs relate to ribbed anchors designed to be fixed to bone via a secondary fixation step. These anchors have axially aligned (one or more) ribs, which are inserted into bone and rotated by applying force on the proximal end of the implant. However, it is believed that such an anchor creates too large of a hole in the patient's bone.

U.S. Pat. No. 4,898,156 to Gattuma et al. relates to an implant having a resilient elastic rib attached to a coupling member. As characterized, the elastic rib causes a toggle or rotation of the anchor in the bone upon insertion. However, since the anchor is not configured to be rotated by a secondary fixation step (e.g., a rotation step), it is believed that the effectiveness of such an anchor depends on the quality of bone within which the anchor is inserted.

U.S. Pat. Nos. 5,540,718, 5,782,863, 5,871,503, 5,879,372, 6,146,408, and 6,306,158 to Bartlett relate to methods of causing off axis rotation of a suture anchor within bone. The methods require the use of an insertion tool having an elastic distal end for initiating a toggle of the anchor upon insertion of the anchor into bone. When implanted in good quality bone, the anchor and bone hole interface purportedly impart a frictional force, which causes the elastic tip of the insertion tool to bend, thereby causing the anchor to toggle and fix to the bone. However, it is believed that an insufficient frictional force may be generated if the anchor is inserted into poor quality bone.

Due to the limitations of the conventional suture anchors, delivery instruments, and methods described above, a need exists for a simple, strong, and reliable suture anchor, as well as a technique for fixating suture to bone.

Furthermore, a need exists for a push-in type suture anchor and delivery instrument that protects the sutures during insertion of the anchor into bone.

SUMMARY OF THE INVENTION

It is an object of the present invention to overcome the disadvantages of conventional suture implants by providing a suture implant capable of being effectively and reliably fixated into various types of bone tissue (e.g., hard, soft, poor, old, etc.). For this purpose, the present invention provides a toggling suture anchor for anchoring at least one suture thread to a bone, the toggling suture anchor being anchored by operation of an insertion tool, the suture anchor including: a shaft having a longitudinal axis, a distal end, a proximal end, and at least one eyelet hole to receive the suture thread; and at least one locking wing extending radially from the shaft, the locking wing being provided on one side of a first plane, the first plane including the longitudinal axis of the suture anchor.

It is another object of the present invention to provide an insertion tool for inserting a suture anchor into bone for anchoring at least one suture thread to the bone, the suture anchor including at least one radially extending wing, the insertion tool including a cylindrically shaped distal receiving end having an interface surface configured to engage with an engagement surface of the suture anchor; a handle coupled to the cylindrically shaped distal receiving end; and an S-shaped slot including a distal portion appropriately dimensioned for loosely receiving the radially extending wing of the suture anchor, and further including an angularly offset proximal portion configured to receive the suture thread, the proximal portion of the S-shaped slot forming a suture guide hub.

It is still another object of the present invention to provide a method of inserting a suture anchor into bone using an insertion tool, the suture anchor including a shaft having a longitudinal axis, a distal end, a proximal end, and at least one eyelet hole to receive at least one suture thread; and at least one locking wing extending radially from the shaft, the locking wing being provided on one side of a first plane, the first plane including the longitudinal axis of the suture anchor, the method including coupling the suture anchor to the insertion tool; inserting the suture anchor into a site in the bone using the insertion tool; applying a rotational force to the insertion tool to rotate the suture anchor within the bone; removing the insertion tool from the bone; and toggling the suture anchor into a final locked position.

DETAILED DESCRIPTION

Figure 1:
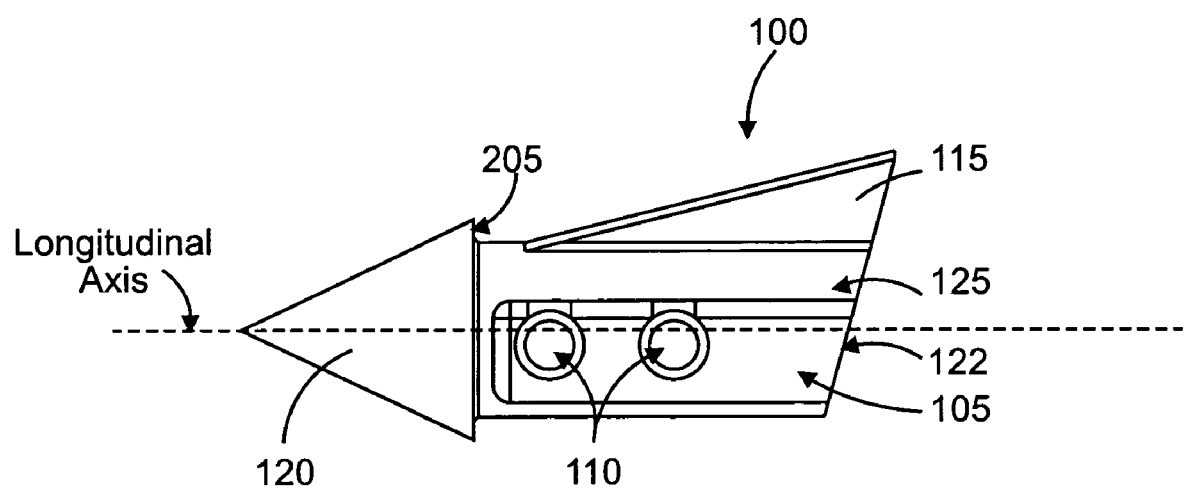
FIG. 1 is a side view of a first exemplary suture anchor according to the present invention.
Figure 2:
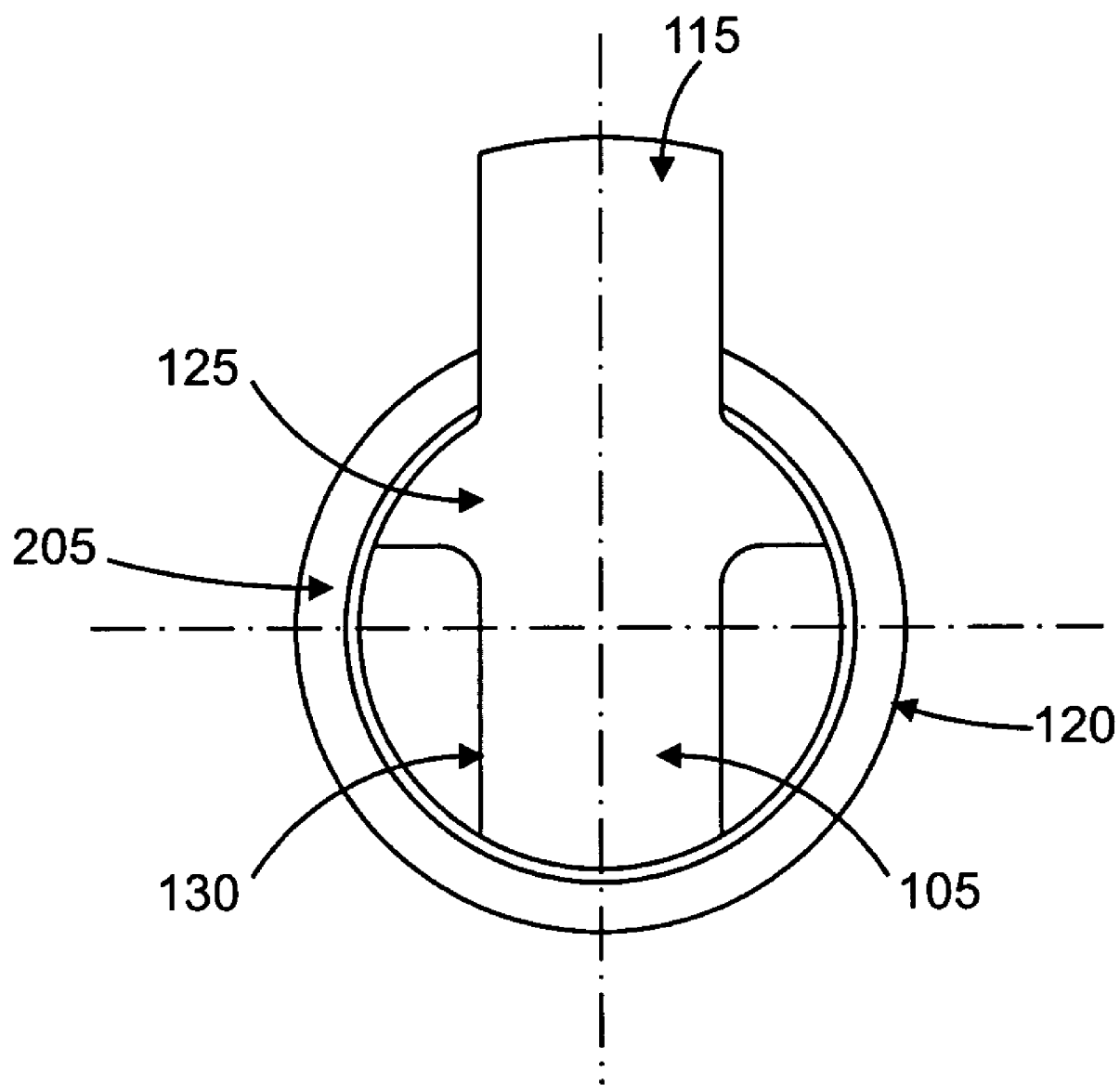
FIG. 2 is aback view of the exemplary suture anchor illustrated in FIG. 1.

Referring now to FIGS. 1 and 2, there are seen side and back views, respectively, of a first exemplary toggle anchor 100 according to the present invention. Toggle anchor 100 includes a shaft 105 having a cone shaped distal end 120, a proximal end 122, at least one eyelet hole 110 for respectively receiving at least one suture thread (not shown), a locking wing 115 extending radially from shaft 105, at least one stabilizing rib 125 (two are shown in FIG. 2) for stabilizing anchor 100 when coupled to an insertion tool (not shown), and a pair of suture grooves 130 for providing a location to guide the suture thread (not shown) during insertion. As shown in FIG. 2, distal end 120 of toggle anchor 100 is provided with an engagement surface 205 configured to be acted upon by an interface surface (not shown) of the insertion tool for insertion of the anchor 100 into bone tissue.

Toggle anchor 100 may be constructed from any materials suitable for implantation into living bone tissue. For example, toggle anchor 100 may include a non-toxic, biocompatible polymer, polymer alloy, fiber reinforced polymer composite, a metal, ceramic, copolymer, polymer mixture, and/or a bio-absorbable material, such as a self-reinforced bio-absorbable copolymer. Furthermore, toggle anchor 100 may be constructed, for example, using fabrication methods described in U.S. Pat. No. 4,968,317 and U.S. Pat. No. 4,898,186, the contents of both of which are expressly incorporated herein by reference.

Furthermore, the width and/or length of toggle anchor 100 may be suitably selected for insertion into a particular type of bone tissue, for example, bone tissue of the rotator cuff. This may be necessary, since the width of respective cancellous layers of different types of bone tissue may vary. Thus, if suture anchor 100 is to be inserted into bone tissue having a relatively thick cancellous layer, suture anchor 100 may be designed to have a longer length. Conversely, if cancellous layer is very thin, suture anchor 100 may be designed shorter in length. In accordance with one exemplary embodiment according to the present invention, for example, the length of toggle anchor 100 is approximately 10.5 mm and the width is approximately 3.5 mm.

Figure 3A:
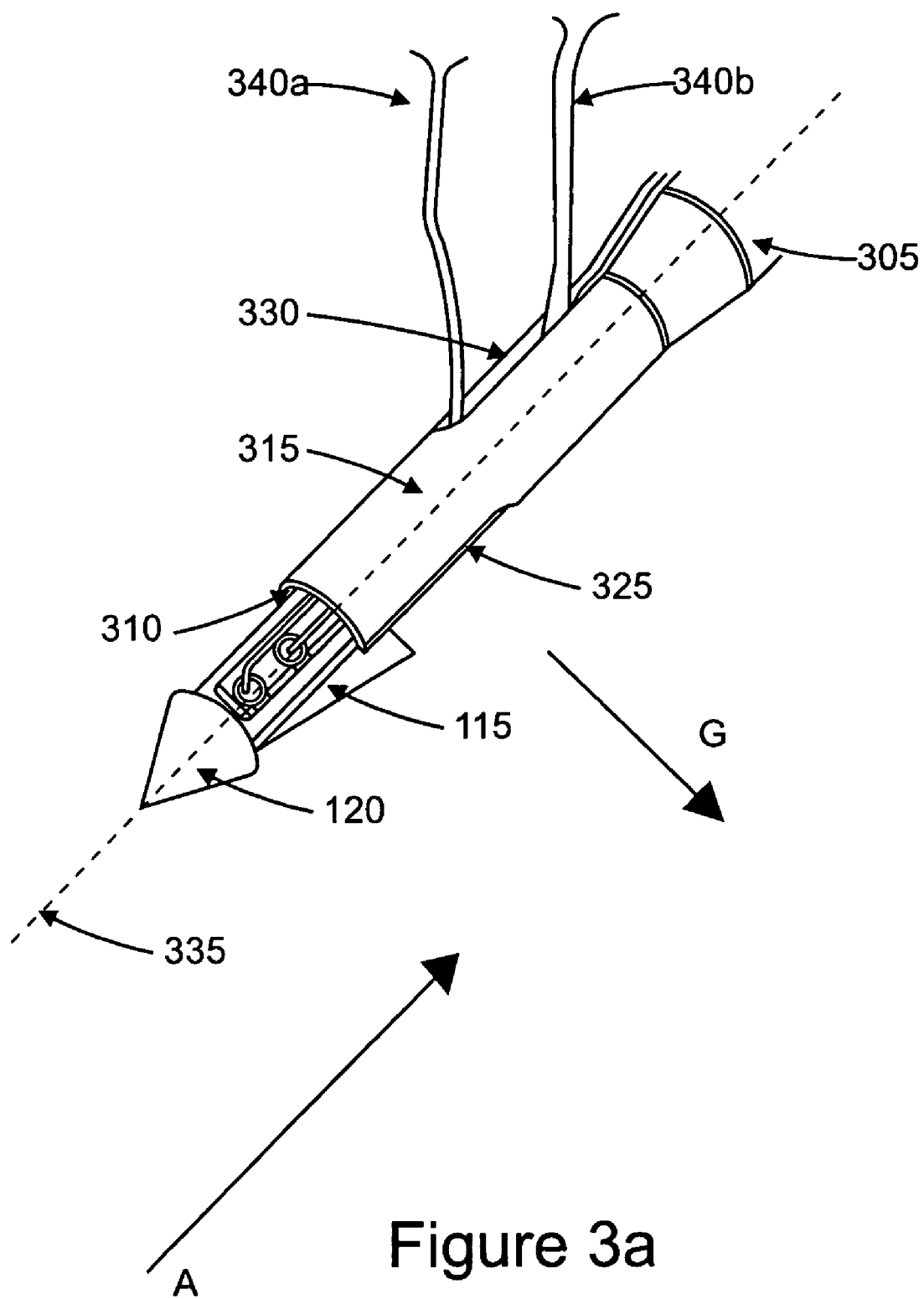
FIGS. 3a-3b show an operational sequence for coupling an exemplary suture anchor according to the present invention to an insertion tool.
Figure 3B:
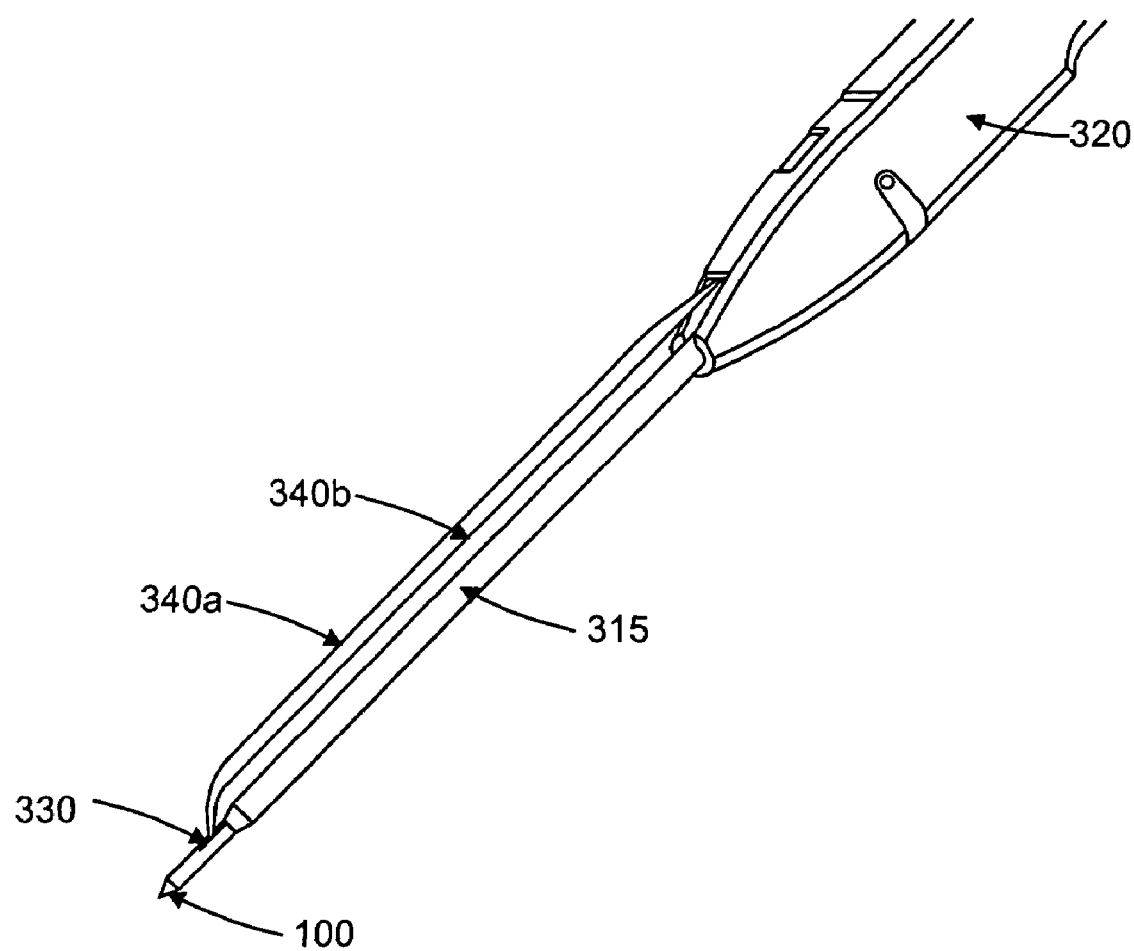

Before being inserted into living bone tissue (not shown), toggle anchor 100 must first be coupled to an appropriately configured insertion tool, such as the various exemplary insertion tools described in co-pending U.S. patent application Ser. No. 10/128,451 entitled DEVICE FOR INSERTING SURGICAL IMPLANTS, the entire contents of which are expressly incorporated herein by reference. Referring now to FIGS. 3a-3b, there is seen an operational sequence for coupling toggle anchor 100 to an insertion tool 305 for inserting anchor 100 into bone tissue. Insertion tool 305 includes a cylindrically shaped distal receiving end 315 having an interface surface 310 for engaging engagement surface 205 of anchor 100, an appropriately dimensioned slot 325 for loosely receiving radially extending wing 115 of anchor 100, and a suture guide 330 formed as a slot in distal receiving end 315 to provide a location for guiding at least one suture thread, for example, suture threads 340a, 340b, to a proximal handle portion 320 configured to be gripped, for example, by a surgeon 405.

As shown in FIG. 3a, toggle anchor 100 is coupled to insertion tool 305 by aligning wing 115 of anchor 100 with slot 325 of insertion tool 305, and then sliding shaft 105 of anchor 100 into cylindrically shaped end 315 of insertion tool 305 along direction A. Coupling of anchor 100 to insertion tool 305 is completed when engagement surface 205 of anchor 100 contacts interface surface 310 of insertion tool 305, as shown in FIG. 3b. Once inserted, stabilizing ribs 125 of anchor 100 contact the inner surface of cylindrical receiving end 315 of insertion tool 305, thereby preventing anchor 100 from sliding perpendicularly to longitudinal axis 335 of insertion tool 305 along direction G.

As shown in FIGS. 3a and 3b, suture threads 340a, 340b extend along suture grooves 130 of anchor 100, through cylindrical receiving end 315, and out through suture guide slot 330 of insertion tool 305. From suture guide slot 330, suture threads 340a, 340b extend along the outer surface of cylindrical receiving end 315 to handle 320. In this manner, cylindrical receiving end 315 protects suture threads 340a, 340b from the frictional forces generated while anchor 100 is being inserted into bone tissue.

Alternatively, it should be appreciated that suture guide slot 330 of insertion tool 305 may be provided further proximally along cylindrical receiving end 315 toward handle 320, or suture guide slot 330 may be dispensed with completely, with suture threads 340a, 340b extending entirely within cylindrically receiving end 315 to handle portion 320 of insertion tool 305. In this manner, suture threads 340a, 340b may be better protected from the frictional forces generated while anchor 100 is being inserted into bone tissue.

Figure 4A:
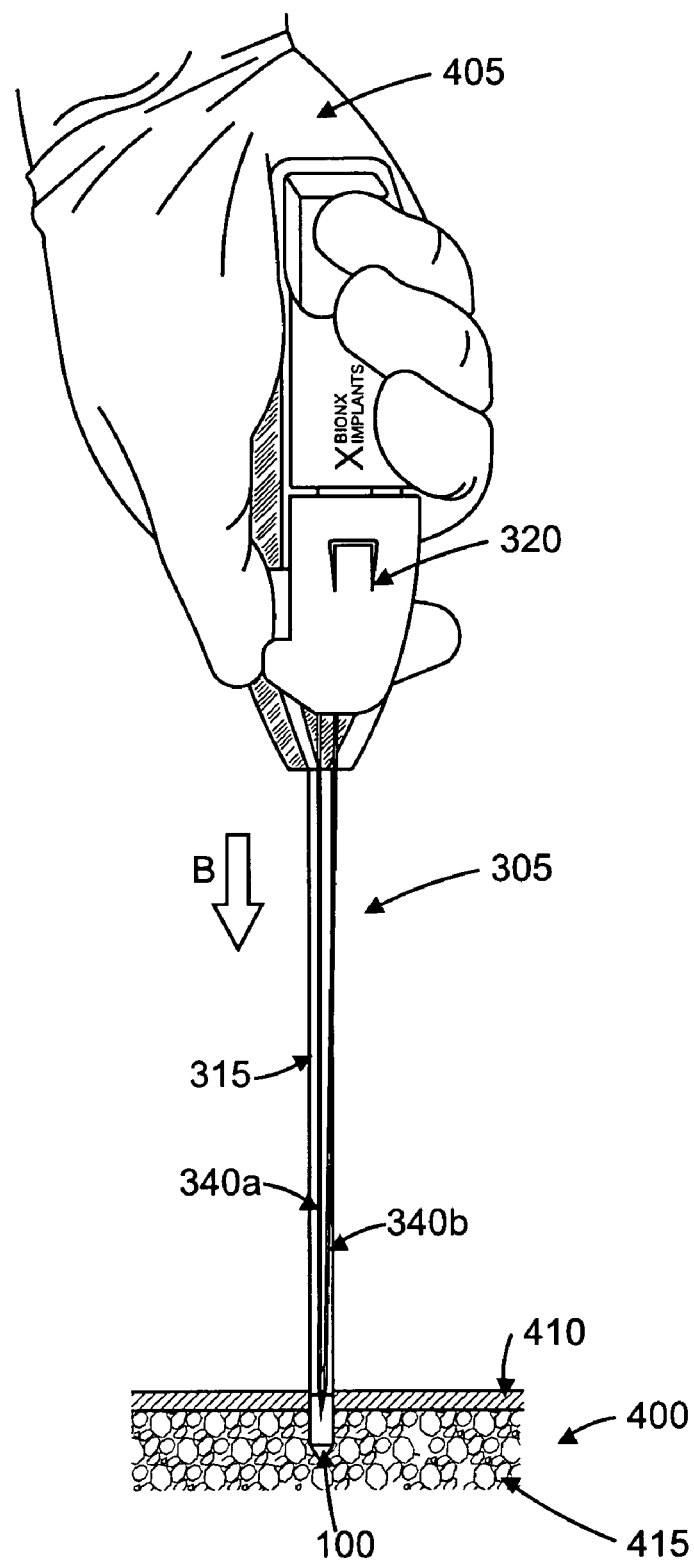
FIGS. 4a-4e show an operational sequence for inserting an exemplary suture anchor according to the present invention into bone tissue.

Once properly coupled to insertion tool 305, anchor 100 may be inserted into bone tissue for providing an anchoring site for suture threads 340a, 340b. Referring now to FIGS. 4a through 4e, there is seen an operational sequence for inserting anchor 100 into bone tissue 400. As shown in FIG. 4a, a user, for example, surgeon 405, inserts anchor 100 through a cortical layer 410 of bone tissue 400 and into a cancellous layer 415 by applying an axial force to insertion tool 305 along direction B. The axial force may be generated, for example, by pushing insertion tool 305 along direction B or, alternatively, may be generated by tapping on handle 320 of insertion tool 305 along direction B with an appropriately configured tapping tool, such as a surgical hammer. In this manner, interface surface 310 of cylindrically receiving end 315 provides a downward force on engagement surface 205 of anchor 100, thereby causing anchor 100 to penetrate bone tissue 400. Alternately, bone tissue 400 may be pre-drilled, as more fully described below.

By providing engagement surface 205 toward distal end 120 of anchor 100, anchor 100 is better stabilized during insertion along a straight trajectory B into bone tissue 400. That is, anchor 100 is better prevented from deviating from a straight-line trajectory during insertion, which may occur with conventional insertion tools that apply the insertion force at the proximal end of an anchor. However, it should be appreciated that the present invention is not limited to suture anchors having distally arranged engagement surfaces. Thus, suture anchor 100 may include an engagement surface located, for example, more proximally along shaft 105, for example, in the vicinity of proximal end 122.

Figure 4B:
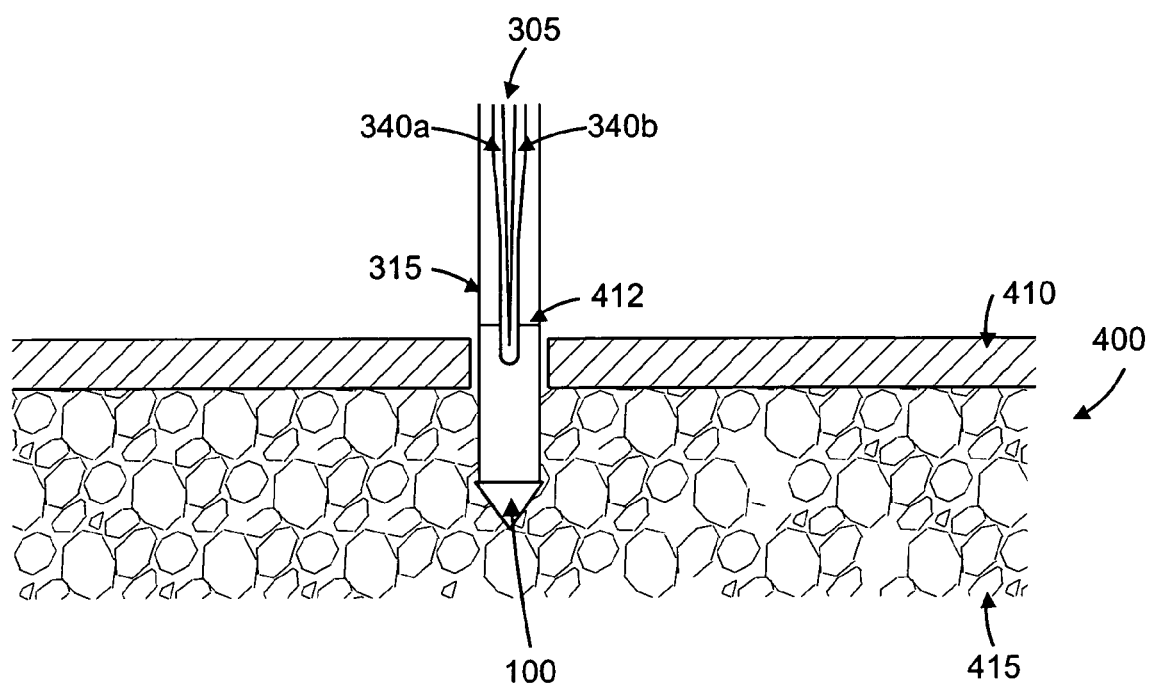

To ensure that anchor 100 is inserted to the proper depth within bone tissue 400, anchor 100 and/or cylindrical receiving end 315 of insertion tool 305 may be provided with a depth marker 412 (i.e., a laser line 412) operable to permit a user, for example, surgeon 405, to visually determine the correct insertion depth of anchor 100. In this manner, surgeon 405 may cease providing the insertion force along direction B once the depth marker is aligned with, for example, the upper surface of cortical layer 410 of bone tissue 400, as shown in FIG. 4b. It should be appreciated that, although FIG. 4b shows insertion tool 305 provided with a single laser line 412, insertion tool 305 and/or anchor 100 may be provided with multiple laser lines for marking appropriate insertion depths for various types of bone, such as the humerus and glenoid bones.

Figure 4C:
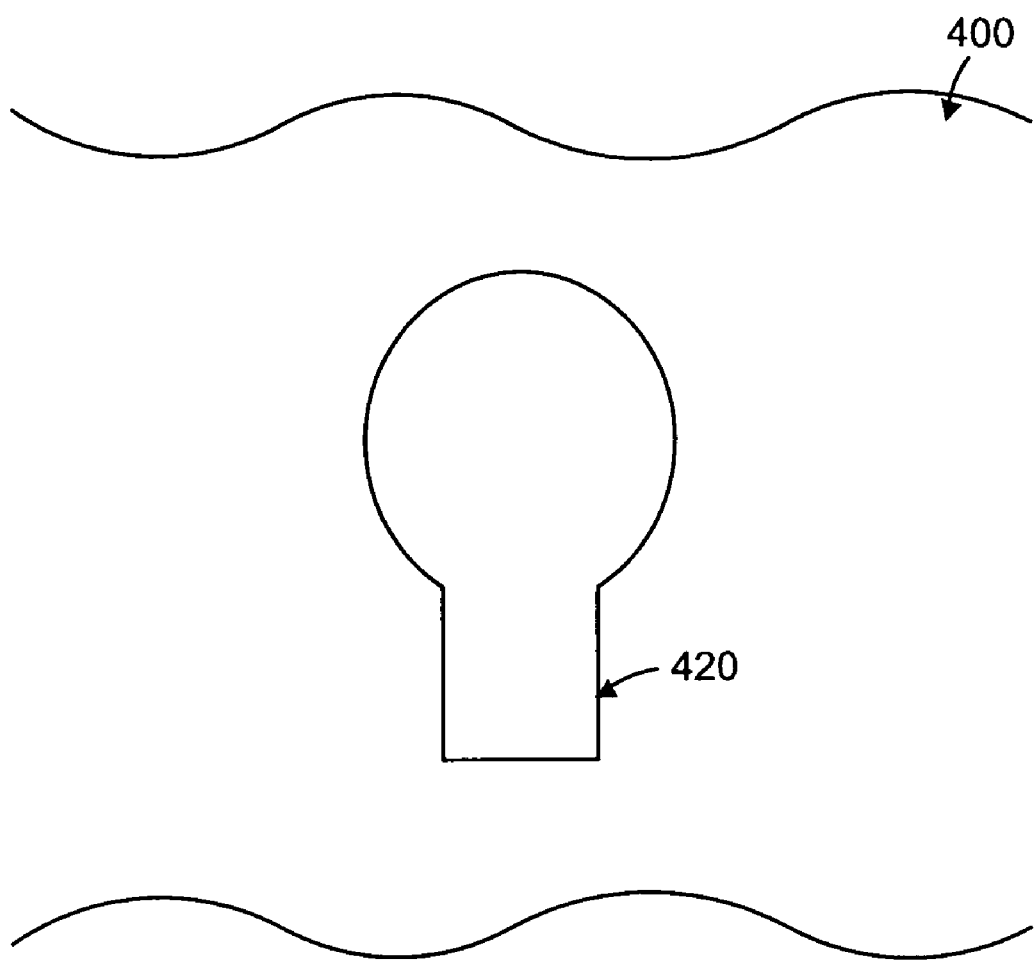

The various embodiments of the present invention permit anchor 100 to be inserted directly into bone tissue 400, or to be inserted into a pre-drilled hole (i.e., a pre-tapped hole) for easier insertion, for example, a pre-drilled hole having a 2.9 mm diameter and a 20 mm insertion depth. In either case, as shown in FIG. 4c, wing 115 of anchor 100 operates to form a radial slot 420 in bone tissue 400 as anchor 100 is inserted into bone tissue 400. It should be appreciated that, if anchor 100 is to be inserted directly into bone tissue 400 without first forming a pre-drilled hole, anchor 100 should be constructed from materials, for example, metal, which are capable of withstanding the additional frictional forces generated during insertion.

Anchor 100 may be inserted through a soft tissue layer before being inserted intone bone tissue 400. In this manner, suture threads 340a, 340b thread through the soft tissue as anchor 100 is inserted into bone tissue 400. Alternatively, however, anchor 100 may be inserted directly into bone tissue 400, with suture threads 340a, 340b being threaded through the soft tissue after insertion. For this purpose, the user, for example, surgeon 405, may thread suture threads 340a, 340b through the soft tissue using a suture needle.

Figure 4D:
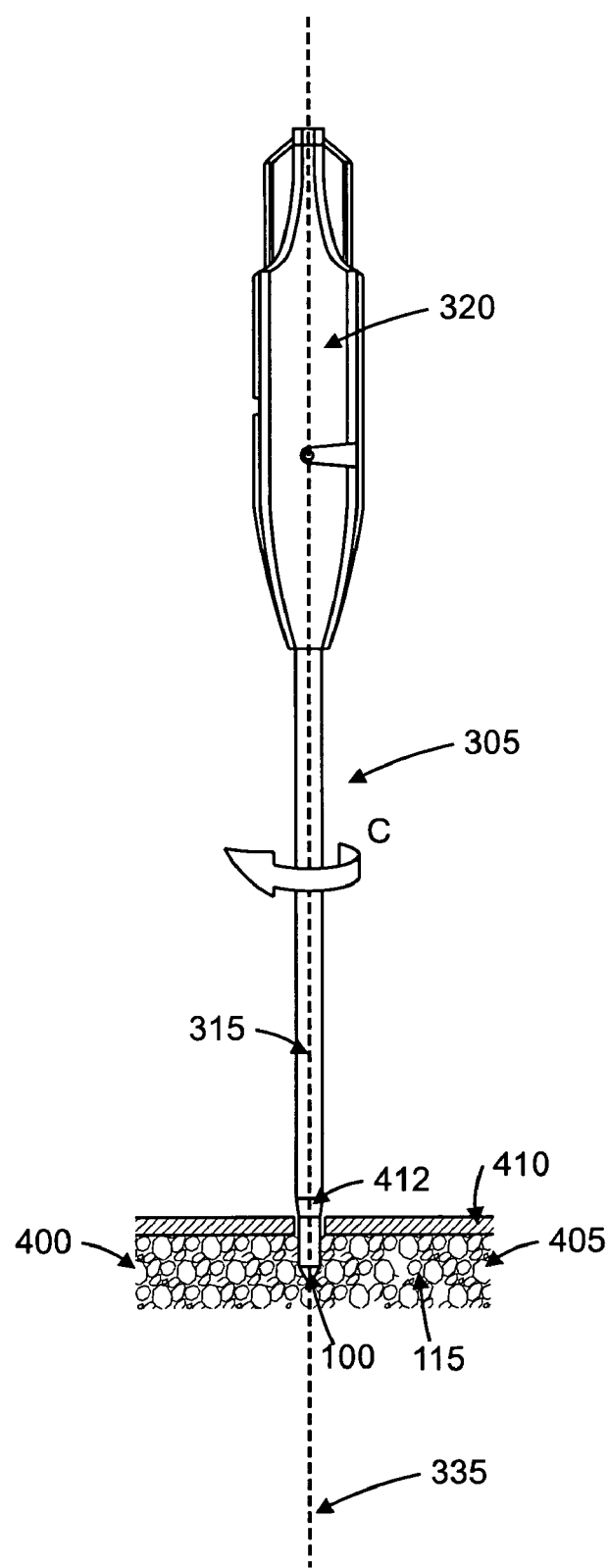
Figure 4E:
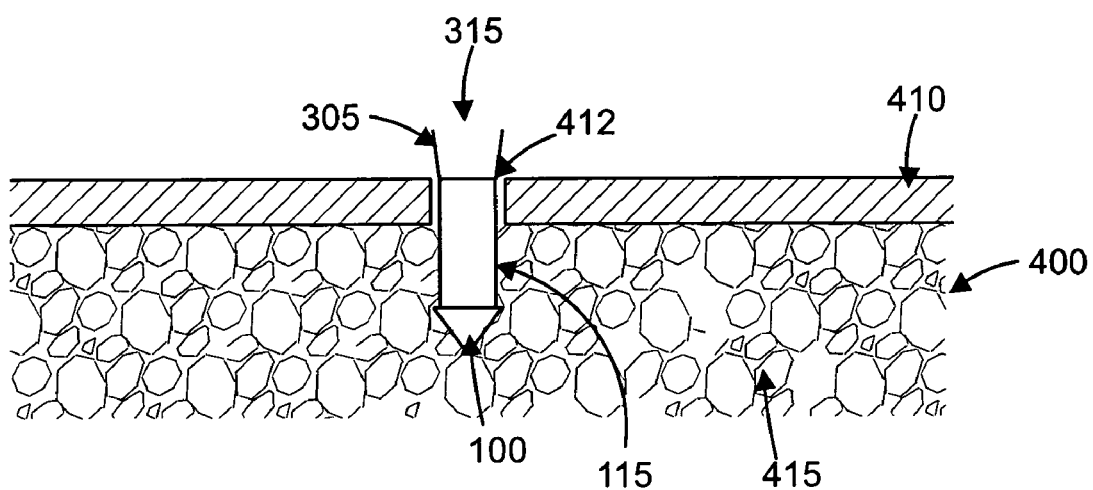

Once anchor 100 is inserted through cortical layer 410 and into soft cancellous layer 415 of bone tissue 400, a rotational force is applied to handle portion 320 of insertion tool 305, thereby causing anchor 100 to rotate along direction C about longitudinal axis 335 of insertion tool 305, as shown in FIGS. 4d and 4e. For this purpose, insertion tool 305 may be rotated through any angle suitable to misalign wing 115 with slot 420 of the bone tissue 400. For example, insertion tool 305 may be rotated approximately ninety degrees. In this manner, radial wing 115 of anchor 100 is caused to misalign with slot 420, thereby preventing anchor 100 from exiting bone tissue 400 when insertion tool 305 is removed and/or while anchor 100 is being toggled into a final locking position, as more fully described below.

Figure 5:
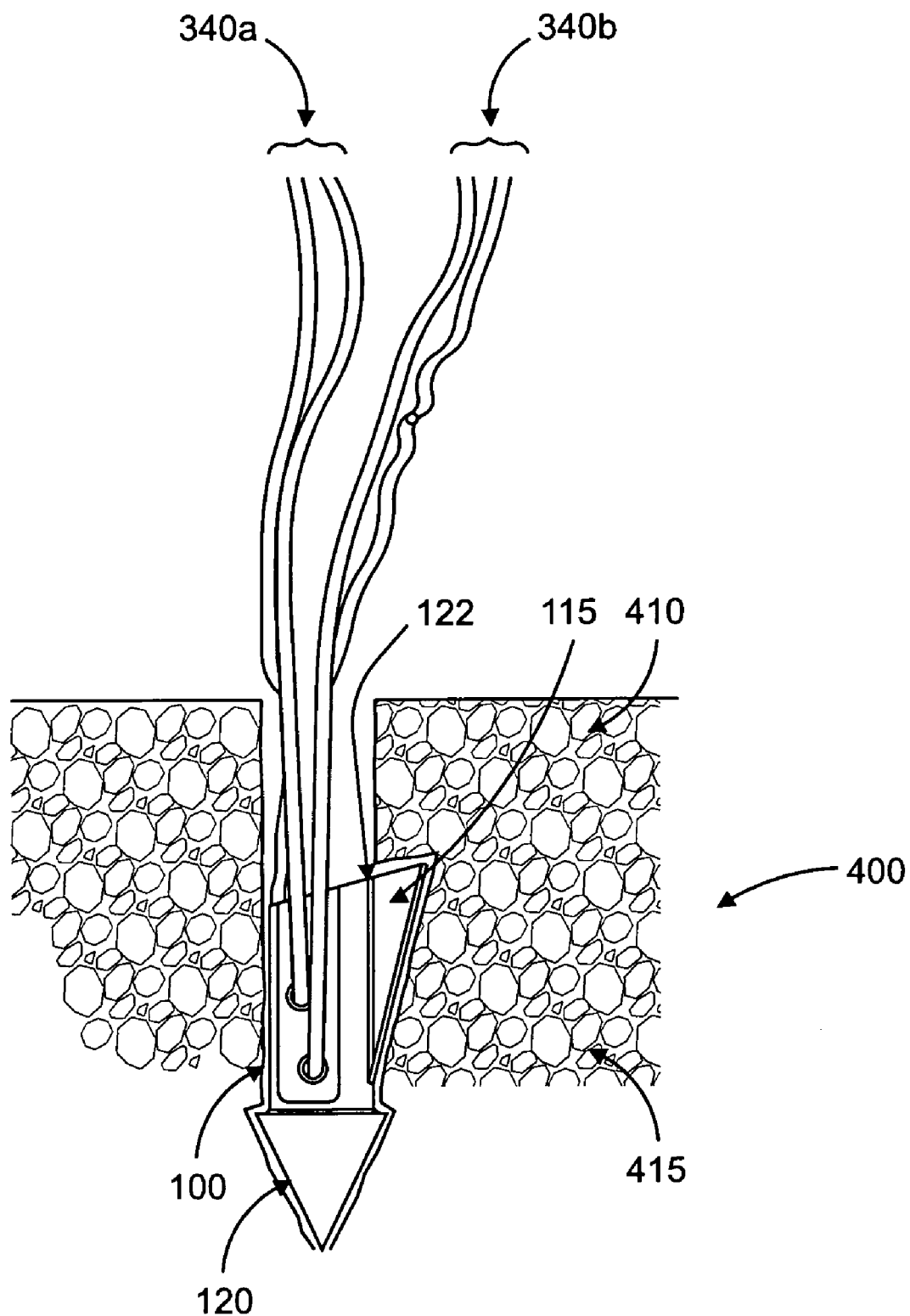
FIG. 5 illustrates an exemplary suture anchor inserted into bone tissue after an insertion tool has been removed.
Figure 6:
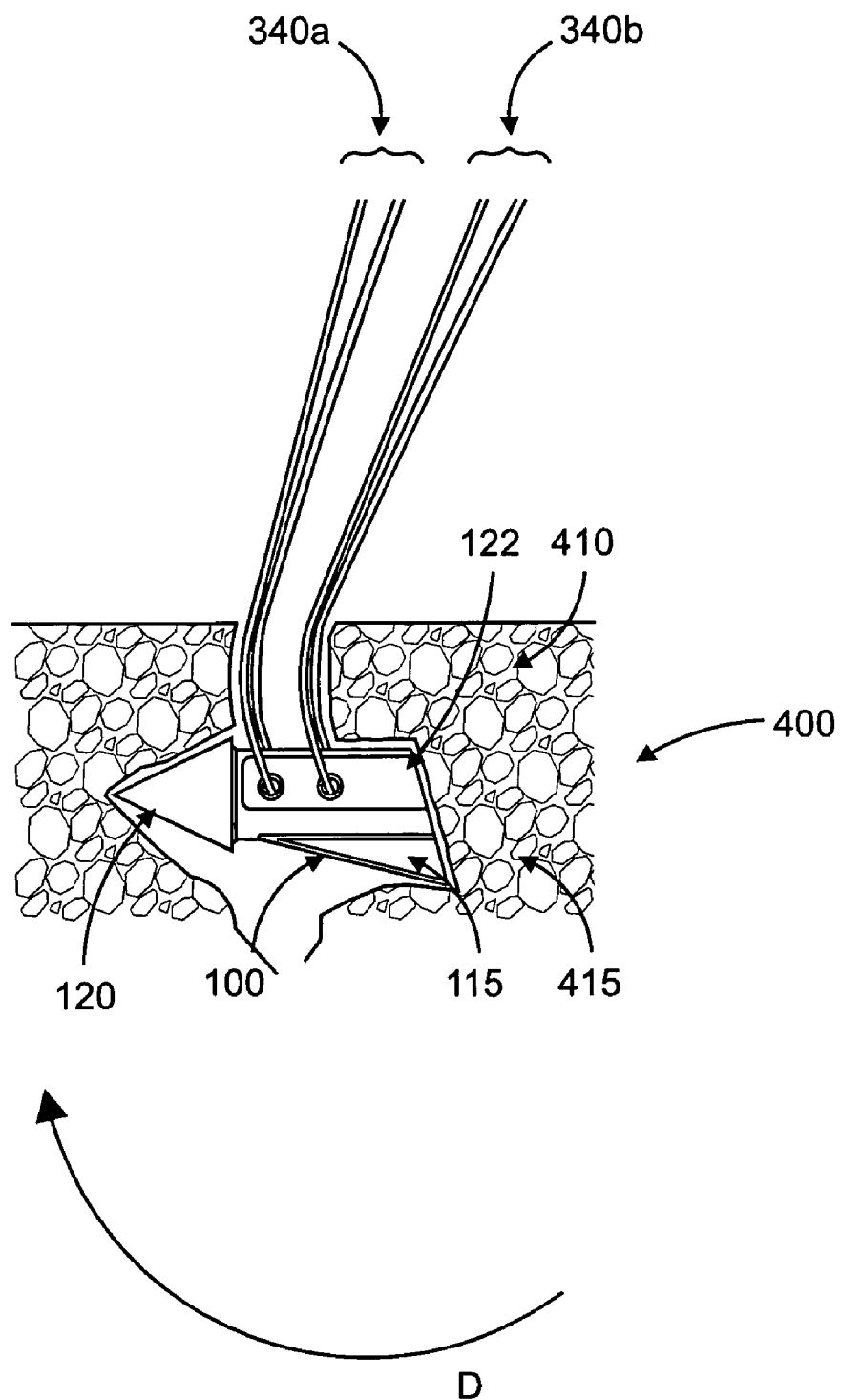
FIG. 6 illustrates the exemplary suture anchor of FIG. 5 toggled into a final locking position.

After anchor 100 is rotated about longitudinal axis 335 of insertion tool 305, insertion tool 305 is removed from bone tissue 400, as shown in FIG. 5. Once insertion tool 305 is removed, anchor 100 is toggled into a final locking position substantially parallel with cortical layer 410 of bone tissue 400, as shown in FIG. 6. For this purpose, suture threads 340a, 340b are tensionally tugged, thereby causing anchor 100 to pivot about the tip of wing 115, as shown by arrow D.

To ease the rotation of anchor 100 about the tip of wing 115, eyelet holes 110 of anchor 100 may be arranged off the longitudinal axis of anchor 100 on the side of shaft 105 facing away from wing 115 (see FIG. 1). In this manner, the distance between eyelet holes 110 and the tip of wing 115 is increased, thereby causing a greater torque to be produced on anchor 100 about the tip of wing 115 when suture threads 340a, 340b are tugged. However, it should be appreciated that eyelet holes 110 need not be arranged off axis and may be arranged, for example, along the longitudinal axis of anchor 100.

To further ease the rotation of anchor 100 about the tip of wing 115, proximal end 122 of anchor 100 may be acutely angled toward distal end 120, with respect to the longitudinal axis of anchor 100, as shown in FIGS. 1, 5, and 6. In this manner, the profile of anchor 100 may be reduced along the circumference of rotation along direction D, thereby reducing the friction produced while anchor 100 is being toggled into the final locking position. As a further advantage, acutely angled distal end 122 reduces the amount of material required to manufacture anchor 100, thereby reducing the amount of foreign material introduced into the body of a patient (not shown). Alternatively, however, it should be appreciated that proximal end 122 of anchor 100 need not be acutely angled, and may, for example, form a ninety degree angle with respect to the longitudinal axis of anchor 100.

In accordance with another exemplary embodiment of the present invention, anchor 100 is constructed from a bio-absorbable material, such as a self-reinforced bio-absorbable copolymer. The bio-absorbable copolymer may, for example, be constructed from a plurality of self-reinforced molecular fiber chains (e.g., polyglycolide fibers), which may be oriented to extend in a predetermined direction with respect to anchor 100. For example, the self-reinforced fibers may be orientated to extend perpendicularly or parallel to the longitudinal axis of anchor 100.

Advantageously, Applicants have found that the ultimate orientation of the molecular fiber chains significantly impacts the strength of eyelet holes 110 as the bio-absorbable material of anchor 100 is metabolized by the body of a patient. This is important, since it is advantageous to prolong the effectiveness of eyelet holes 110 for as long as possible, to better ensure that suture threads 340*a*, 340*b* maintain proximity of the soft tissue to bone 400 for a time sufficient for the soft tissue to naturally adhere itself to bone 400.

Specifically, Applicants have found that orientating the self-reinforced molecular fiber chains in a direction perpendicular to the force produced on the eyelet holes 110 by suture threads 340*a*, 340*b* prolongs the effectiveness of eyelet holes 110. Thus, in accordance with this exemplary embodiment of the present invention, the self-reinforced molecular fiber chains are arranged parallel to the longitudinal axis of anchor 100. In this manner, after anchor 100 is positioned into the final locking position, suture threads 340*a*, 340*b* produce tensional force on eyelet holes 110 in a direction perpendicular to the extension of the self-reinforced molecular fiber chains.

Figure 7A:
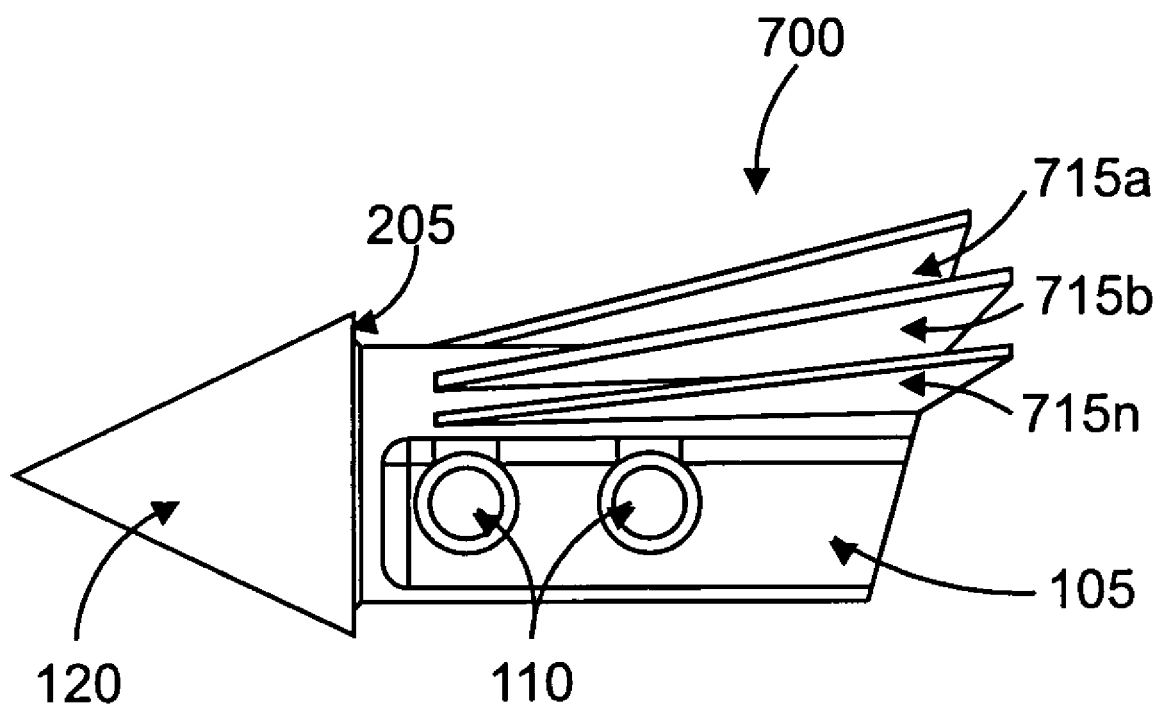
FIGS. 7a-7b illustrate side and back views, respectively, of another exemplary suture anchor according to the present invention.
Figure 7B:
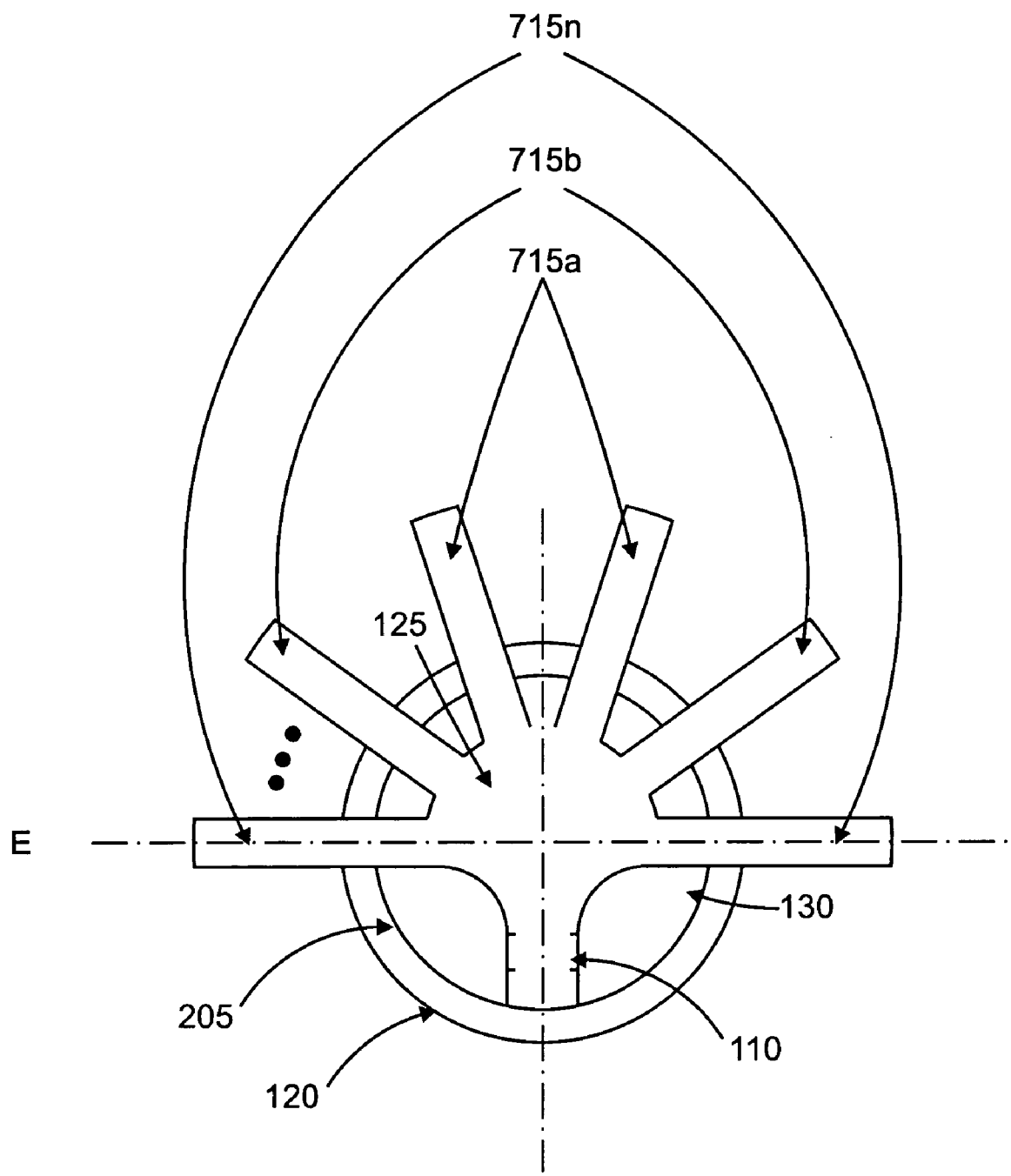

Referring now to FIGS. 7*a* and 7*b*, there are seen side and back views, respectively, of another exemplary toggle anchor 700 according to the present invention. Toggle anchor 700 is similar to toggle anchor 100, except that toggle anchor 700 is provided with a plurality of wing pairs 715*a*, 715*b*, ..., 715*n* arranged symmetrically about plane E and on only one side of plane F, for example, the side of plane F facing away from eyelet holes 110, as shown in FIG. 7*b*. Although not necessary, plane F may be chosen to extend parallel to the axes of the eyelet holes 110, with plane E extending perpendicularly thereto. By providing multiple wing pairs 715*a*, 715*b*, ..., 715*n*, anchor 700 may better grip bone tissue 400 while toggling into the final locked position.

Figure 8:
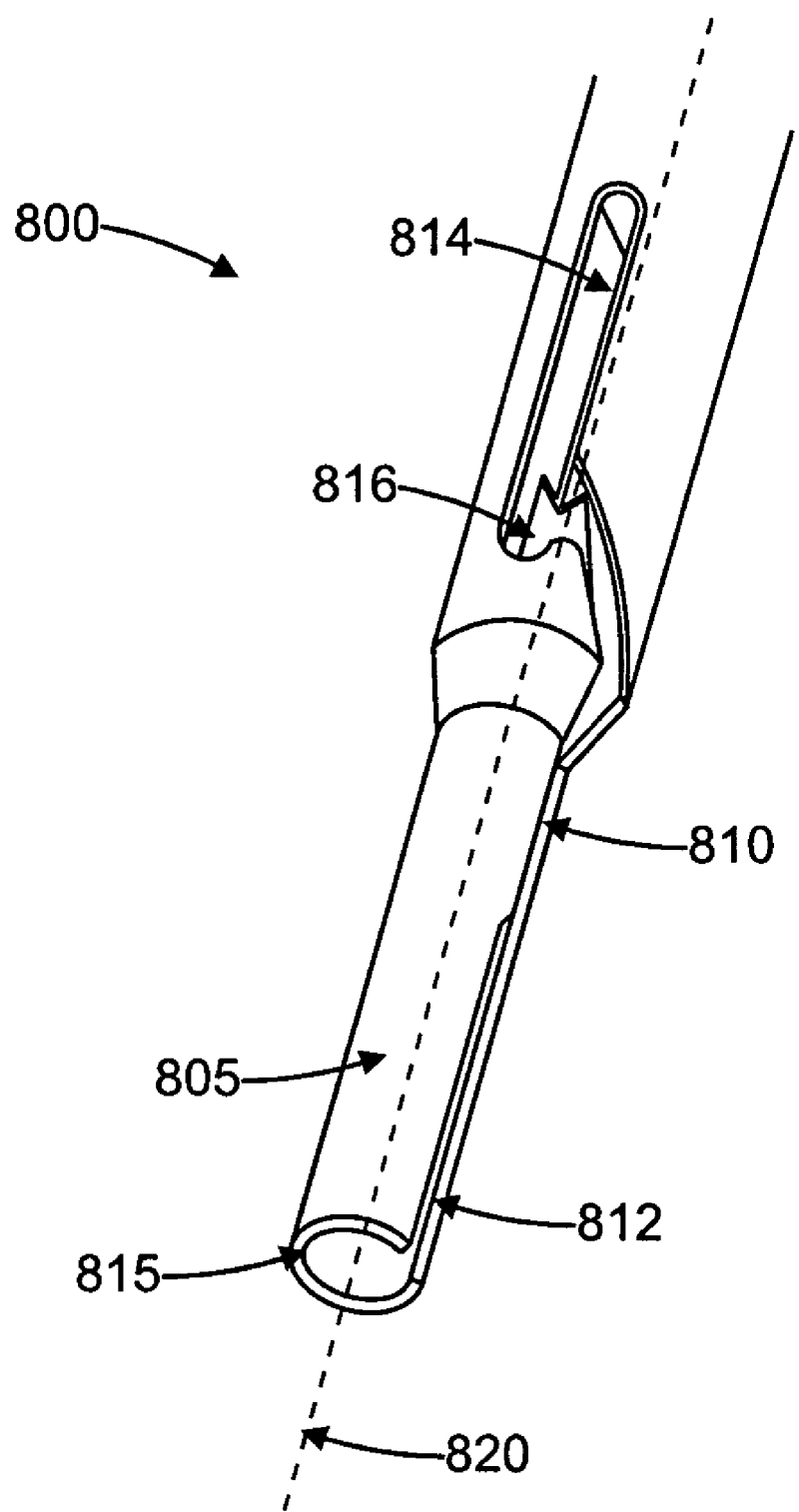
FIG. 8 illustrates an exemplary insertion tool according to the present invention.

Referring now to FIG. 8, there is seen an exemplary insertion tool 800 according to the present invention. Insertion tool 800 includes similar features as insertion tool 305, except that insertion tool 800 includes an S-shaped slot 810 configured to permit insertion tool 800 to insert a plurality of suture anchors, for example, a plurality of suture anchors 100, 700 into bone tissue 400. S-shaped slot 810 includes a distal portion 812 appropriately dimensioned for loosely receiving radially extending wing 115 of suture anchor 100 and an angularly offset proximal portion 814 configured to receive suture threads 340*a*, 340*b*, proximal portion 814 forming a suture guide hub 816.

Similar to the various exemplary embodiments described above, toggle anchor 100 is coupled to insertion tool 800 by sliding shaft 105 of anchor 100 into cylindrically shaped end 805 of insertion tool 800. Coupling of anchor 100 to insertion tool 305 is completed when engagement surface 205 of anchor 100 contacts interface surface 815 of insertion tool 800. Once inserted, stabilizing ribs 125 of anchor 100 contact the inner surface of cylindrically receiving end 805 of insertion tool 800, thereby preventing anchor 100 from sliding in a direction approximately perpendicular to longitudinal axis 820 of insertion tool 800.

Unlike the various exemplary embodiments described above, however, suture threads 340*a*, 340*b* do not extend through cylindrical receiving end 815 and out through a suture guide slot. Rather, suture threads 340*a*, 340*b* extend along distal portion 812 of S-shaped slot 810 to angularly offset proximal portion 814 of S-shaped slot 810. In this manner, insertion tool 800 may be employed to insert a plurality of suture anchors, as more fully described below.

Figure 9A:
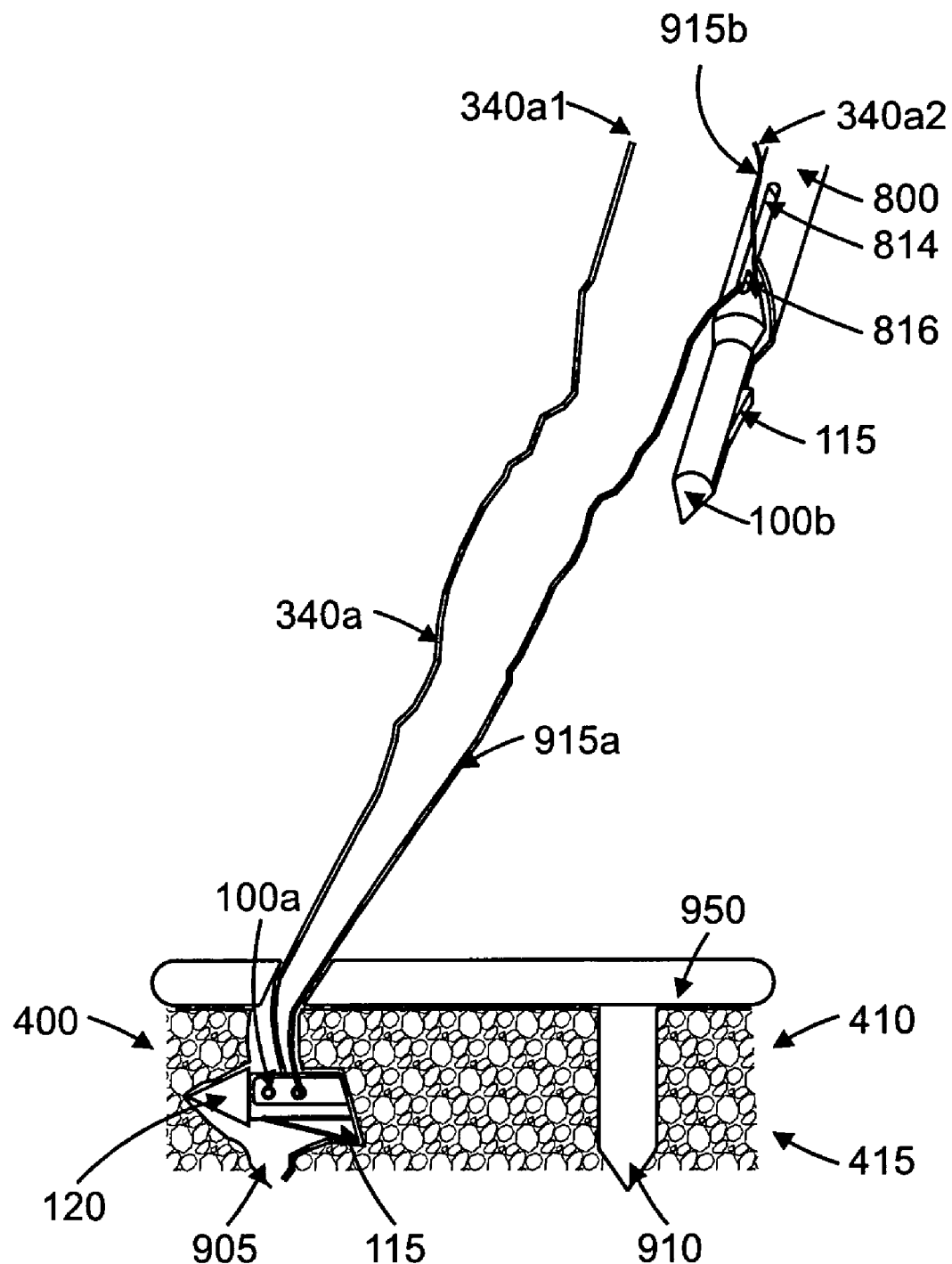
FIGS. 9a-9g show an operational sequence for inserting a plurality of suture anchors into bone tissue using the exemplary insertion tool of FIG. 8.

Referring now to FIGS. 9*a* through 9*g* there is seen an operational sequence for inserting a plurality of suture anchors 100, 700 (suture anchors 100*a* and 100*b* are shown in FIGS. 9*a* through 9*d*) to secure soft tissue 950 to bone tissue 400, using insertion tool 800. Initially, first suture anchor 100*a* is threaded with a single suture thread 340*a* having a first end 340*a*1 and a second end 340*a*2, as shown in FIG. 9*a*. Then, first suture anchor 100*a* is inserted into a first site 905 of bone tissue 400 in a manner similar to the various exemplary embodiments described above, as shown in FIG. 9*a*. Specifically, first suture anchor 100 is inserted into bone tissue 400 in the manner described above with reference to FIGS. 4*a* through 4*e*.

After first suture anchor 100*a* is inserted into bone tissue 400 and insertion tool 800 removed, second end 340*a*2 of suture thread 340*a* is threaded through one of eyelet holes 110 of second suture anchor 100*b*, which is then coupled to insertion tool 800. After coupling second anchor 100*b* to insertion tool 800, distal portion 915*a* of second end 340*a*2 of suture thread 340*a* is guided toward first suture anchor 100*a* via suture guide hub 816, while proximal portion 915*b* of second end 340*a*2 of suture thread 340*a* loosely protrudes through proximal portion 814 of S-shaped slot 810, as shown in FIG. 9*a*.

Figure 9B:
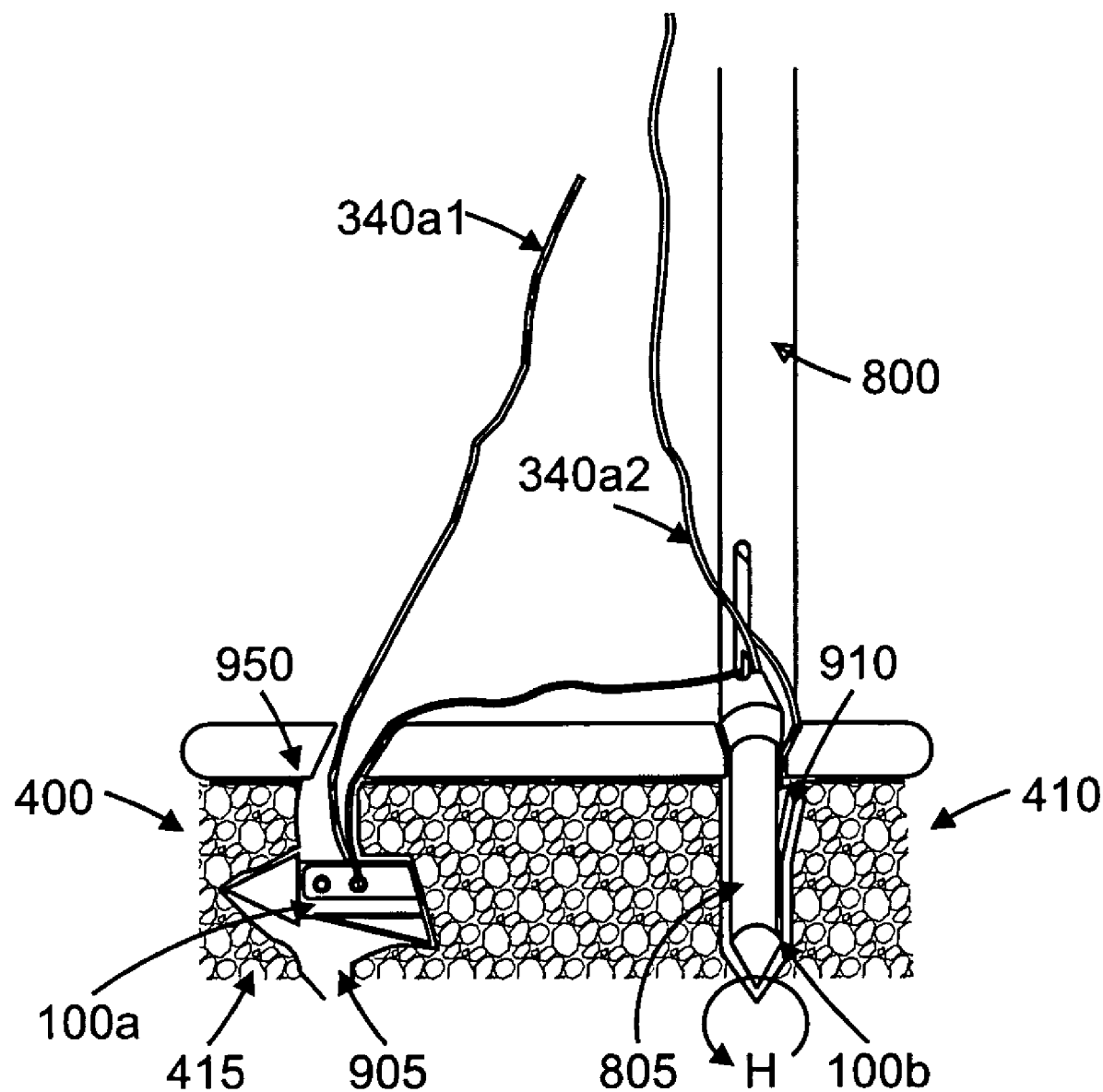
Figure 9C:
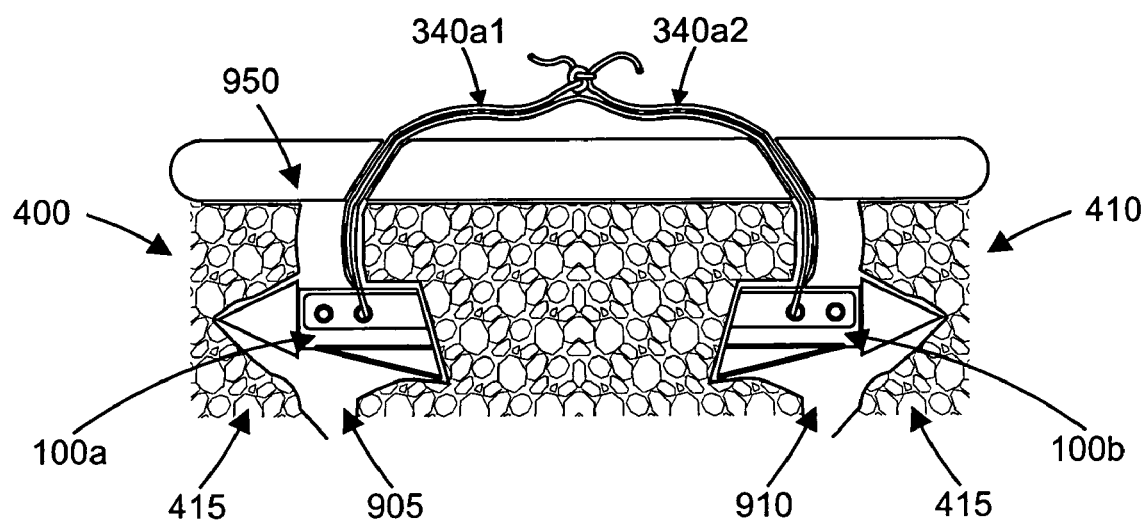
Figure 9D:
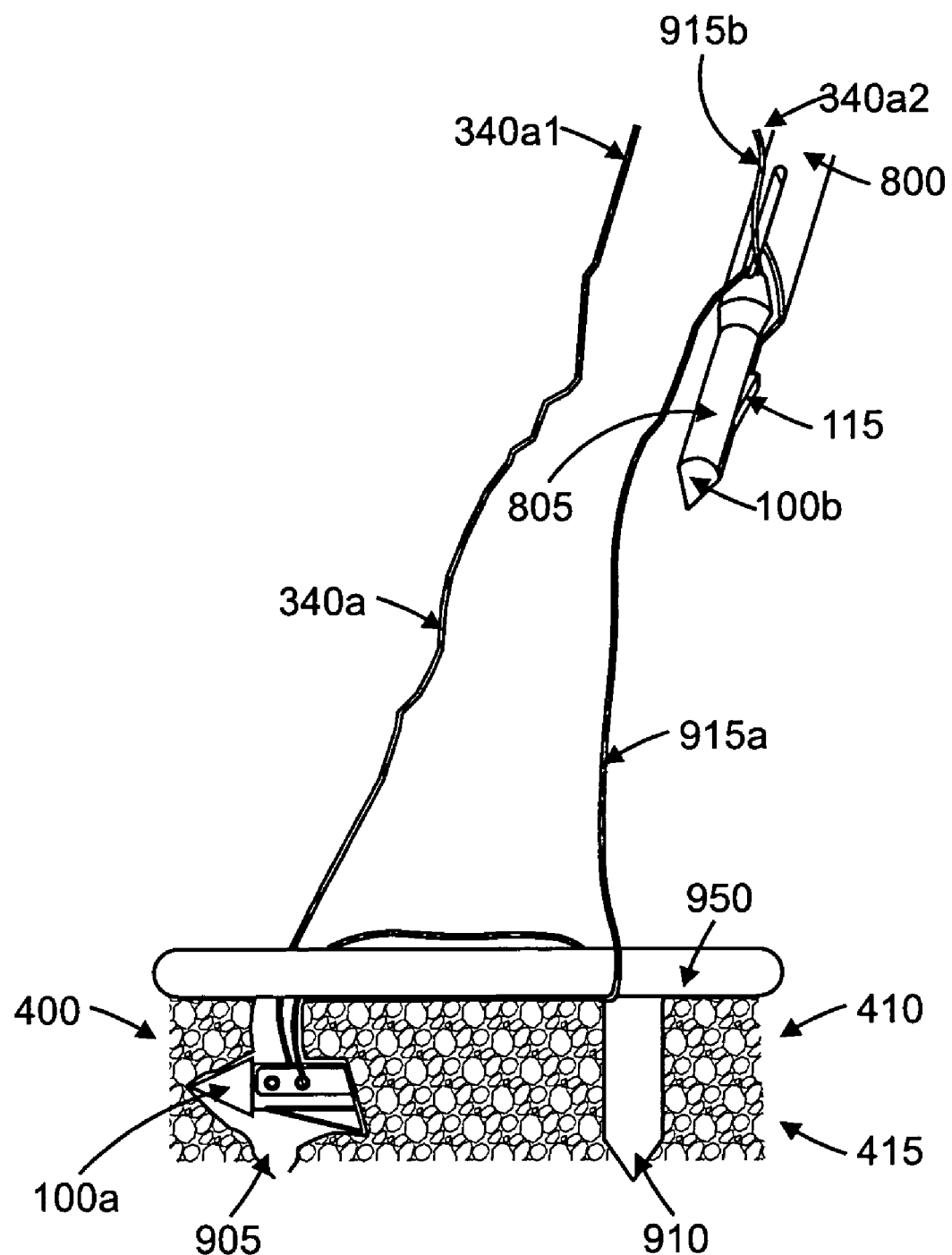

It should be appreciated that distal portion 915*a* of second end 340*a*2 of suture thread 340*a* may be threaded through soft tissue 950 before being threaded through one of eyelet holes 110 of second suture anchor 100*b*, as shown in FIG. 9*d*.

Next, insertion tool 800 is positioned distally for insertion of second anchor 100*b* into second site 910 of bone tissue 400. While positioning insertion tool 800 for this purpose, any resultant slack on distal portion 915 of second end 340*a*2 of suture thread 340*a* may be taken up by tugging on proximal portion 915*b* of second end 340*a*2 loosely protruding through the proximal portion 814 of S-shaped slot 810.

Figure 9E:
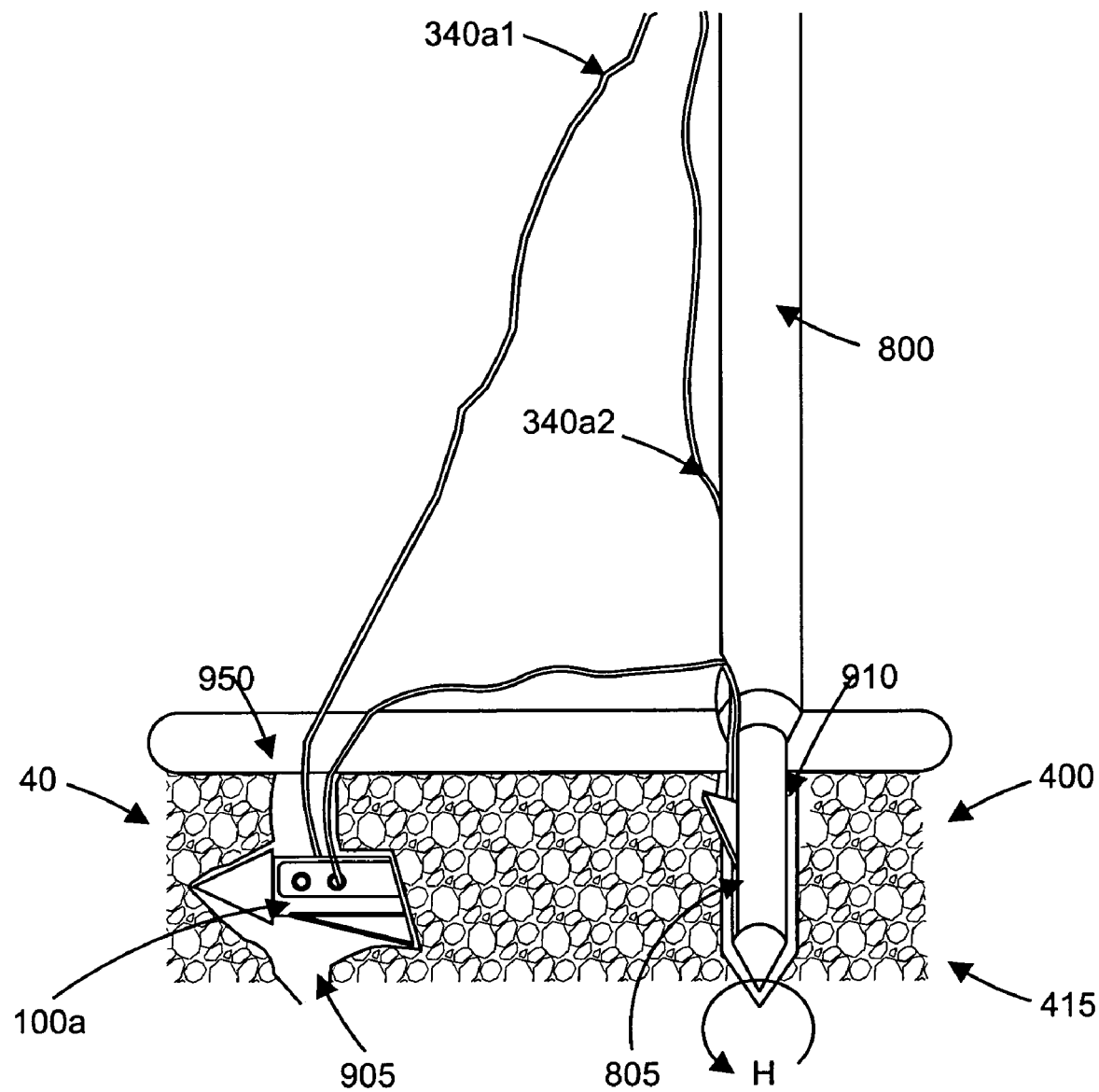

Once insertion tool 800 is properly positioned, second anchor 100*b* is inserted into second site 910 of bone tissue 400, as shown in FIG. 9*b*. As described above, second anchor 100*b* may be inserted through soft tissue 950 before being inserted through bone tissue 400 or, alternatively, may be inserted directly into bone tissue 400, without first traversing soft tissue 950. Similar to the various embodiments described above, second suture anchor 100*b* is then rotated, as shown in FIG. 9*e*, by providing a rotational force to the handle portion (not shown) of insertion tool 800, thereby causing misalignment of wing 115 of anchor 100 with slot 420 to prevent anchor 100*b* from exiting bone tissue 400 when insertion tool 800 is removed and/or while toggling anchor 100*b* into a final locking position. In this exemplary embodiment, the rotation of insertion tool 800 along direction H also causes distal and proximal portions 915*a*, 915*b* of second end 340*a*2 of suture thread 340*a* to align with proximal portion 812 of S-shaped slot 810, thereby permitting insertion tool 800 to be removed from second site 910 of bone tissue 400 without interfering with the suture thread 340*a*.

Figure 9F:
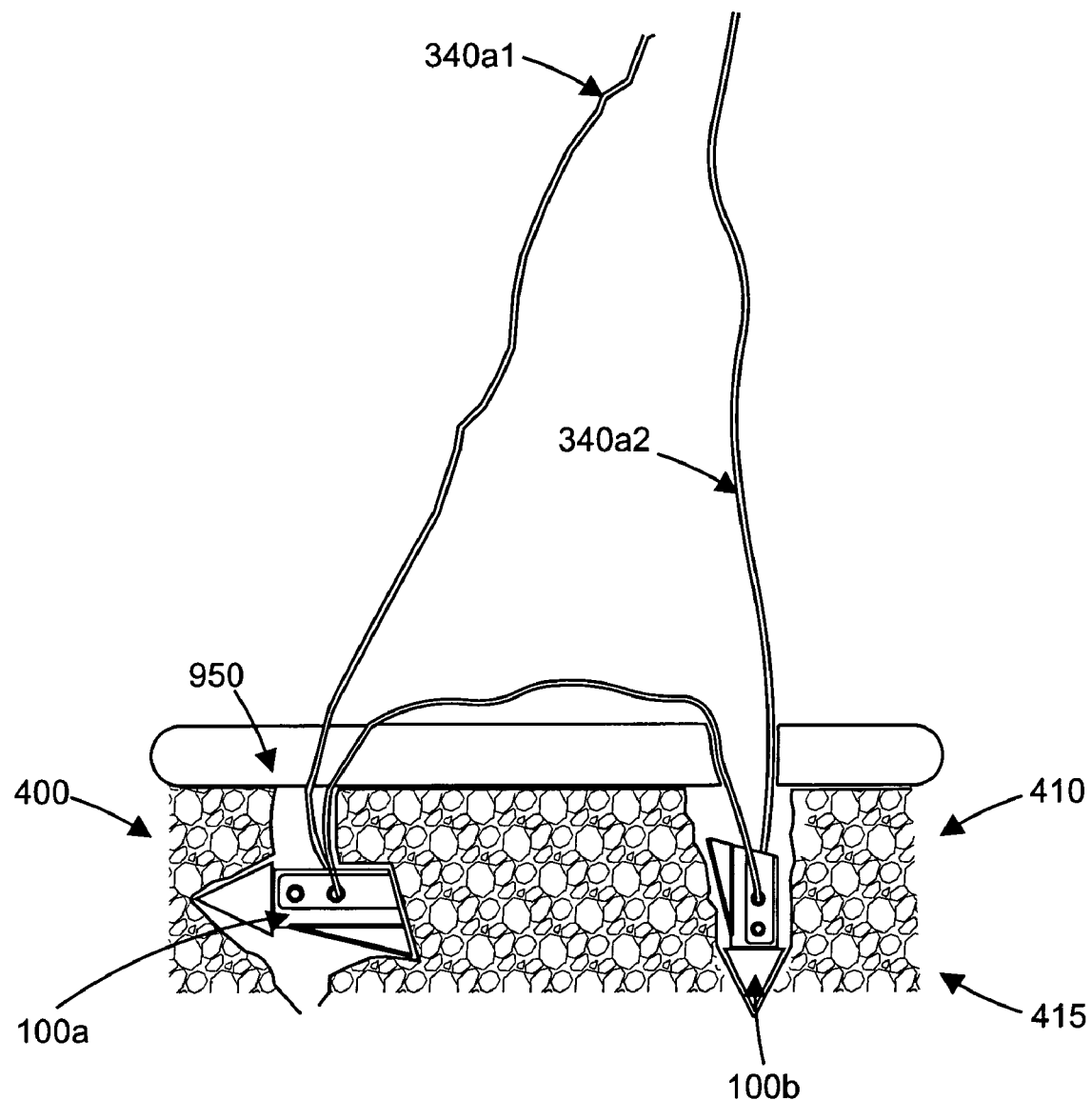
Figure 9G:
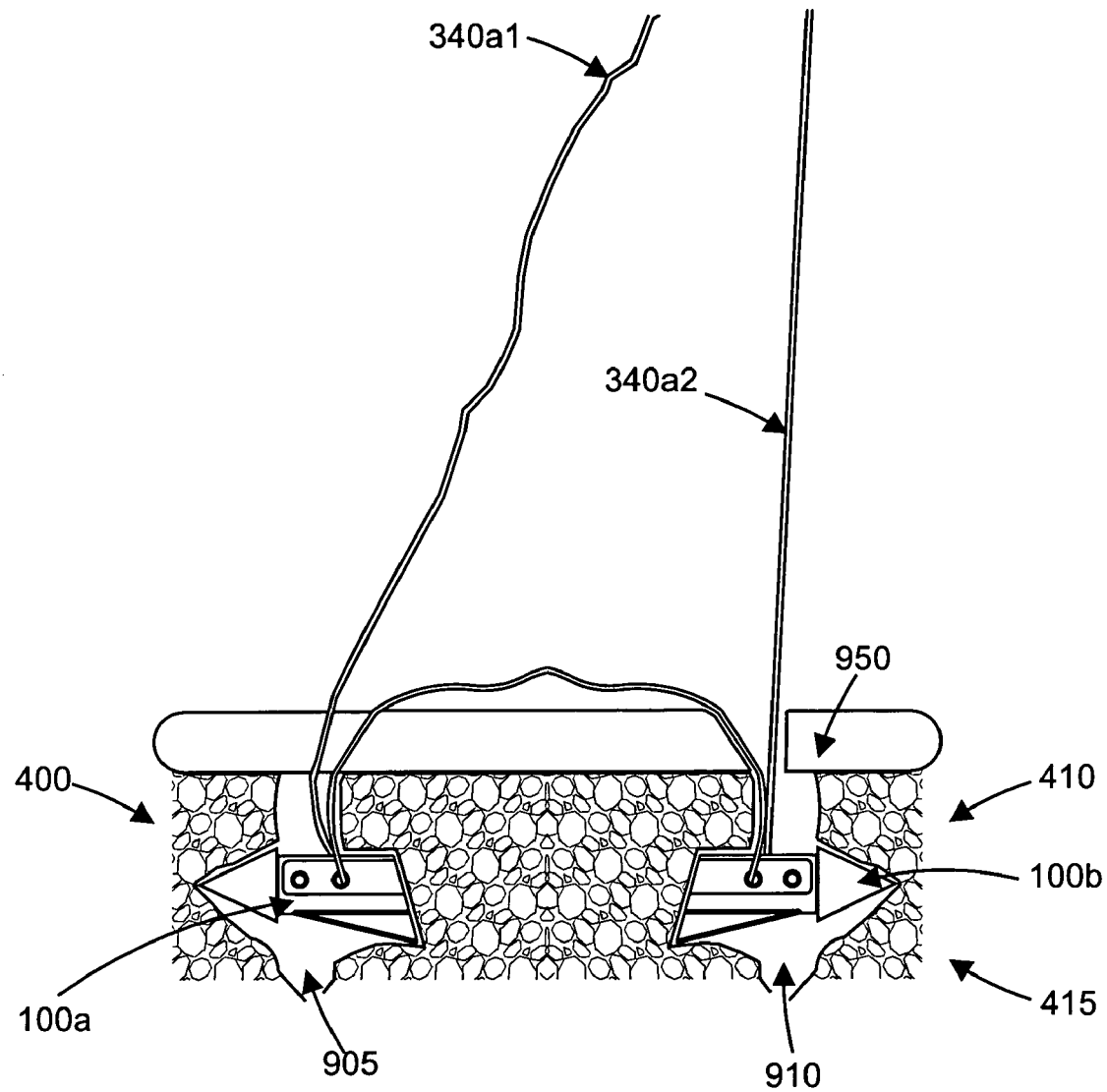

Once insertion tool 800 is removed from second site 910 of bone tissue 400, as shown in FIG. 9*f*, second anchor 100*b* is toggled into the final locking position by tugging on proximal portion 915*b* of second end 340*a*2 of suture thread 340*a*, in a manner similar to the various exemplary embodiments described above, as shown in FIG. 9*g*.

Finally, after second suture anchor 100b is toggled into the final locking position, a user, for example, surgeon 405, may tie together first and second ends 340a1, 340a2 of suture thread 340a to complete the anchoring procedure, as shown in FIG. 9c.

It should be appreciated that, although the above-described operational sequence describes a sequence for the insertion of two suture anchors 100a, 100b, the sequence may be repeated any number of desired times for inserting additional suture anchors, for example, four anchors.

Although the present invention has been described in relation to particular embodiments thereof, many other variations and modifications and other uses will become apparent to those skilled in the art. Therefore, the present invention should be limited not by the specific disclosure herein, but only by the appended claims.

What is claimed is:

1. A toggling suture anchor for anchoring at least one suture thread to a bone, the toggling suture anchor being anchored by operation of an insertion tool having a longitudinal tool axis, the suture anchor comprising:
    a shaft having a longitudinal axis, a distal end, a proximal end, at least one eyelet hole positioned starting at a first distance from the distal end to receive the suture thread, and at least one suture groove extending parallel to the longitudinal axis of the shaft to provide a location to guide the suture thread while inserting the suture anchor into the bone;
    a front part extending from the distal end of the shaft and having an apex on the longitudinal axis and a base having an insertion tool engagement surface, the base being positioned parallel to the distal end of the shaft; and
    at least one locking wing extending radially from the shaft, the at least one locking wing having a narrow end positioned about the first distance from the distal end and a wide end positioned at the proximal end, the locking wing tapering from the narrow end to the wide end being provided on one side of a first plane through the longitudinal axis, wherein during use of the insertion tool to insert the anchor in the bone, the longitudinal tool axis is parallel to the longitudinal axis of the suture anchor.

2. The suture anchor according to claim 1, wherein the engagement surface is configured to engage with an interface surface of the insertion tool.

3. The suture anchor according to claim 2, wherein the front part is cone shaped.

4. The suture anchor according to claim 1, wherein the proximal end of the shaft is acutely angled toward the distal end with respect to the longitudinal axis of the suture anchor.

5. The suture anchor according to claim 1, wherein the at least one locking wing includes a single locking wing extending radially from the shaft.

6. The suture anchor according to claim 5, wherein the engagement surface is configured to engage with an interface surface of the insertion tool.

7. The suture anchor according to claim 6, wherein the front part is cone shaped.

8. The suture anchor according to claim 7, wherein the proximal end of the shaft is acutely angled toward the distal end with respect to the longitudinal axis of the suture anchor.

9. The suture anchor according to claim 1, wherein the at least one eyelet hole is arranged off the longitudinal axis of the suture anchor.

10. The suture anchor according to claim 1, wherein the shaft of the suture anchor further includes at least one stabilizing rib to stabilize the suture anchor when coupled to the insertion tool.

11. The suture anchor according to claim 1, wherein the suture anchor includes at least one of a non-toxic and bio-compatible polymer, a polymer alloy, a fiber reinforced polymer composite, a metal, ceramic, copolymer, polymer mixture, and a bio-absorbable material.

12. A toggling suture anchor for anchoring at least one suture thread to a bone, the toggling suture anchor being anchored by operation of an insertion tool, the suture anchor comprising:
    a shaft having a longitudinal axis, a distal end, a proximal end, at least one eyelet hole to receive the suture, and at least one suture groove extending parallel to the longitudinal axis of the shaft to provide a location to guide the suture thread while inserting the suture anchor into the bone; and
    a front part extending from the distal end of the shaft and having an apex on the longitudinal axis and a base having an insertion tool engagement surface, the base being positioned parallel to the distal end of the shaft, wherein the distal end of the shaft is perpendicular with respect to the longitudinal axis and the proximal end of the shaft is acutely angled toward the distal end with respect to the longitudinal axis of the suture anchor.

13. The suture anchor according to claim 12, wherein the engagement surface is configured to engage with an interface surface of the insertion tool.

14. The suture anchor according to claim 13, wherein the front part is cone shaped.

15. The suture anchor according to claim 12, wherein the shaft of the suture anchor further includes at least one stabilizing rib to stabilize the suture anchor when coupled to the insertion tool.

16. The suture anchor according to claim 12, wherein the suture anchor includes at least one of a non-toxic and bio-compatible polymer, a polymer alloy, a fiber reinforced polymer composite, a metal, ceramic, copolymer, polymer mixture, and a bio-absorbable material.

17. A toggling suture anchor for anchoring at least one suture thread to a bone, the toggling suture anchor being anchored by operation of an insertion tool, the suture anchor comprising:
    a shaft having a longitudinal axis, a distal end, a proximal end, at least one eyelet hole positioned starting at a first distance from the distal end to receive the suture thread, and at least one stabilizing rib configured to contact an inner surface of a cylindrical distal end of the insertion tool to stabilize the suture anchor when coupled to the insertion tool;
    a front part extending from the distal end of the shaft and having an apex on the longitudinal axis and a base having an insertion tool engagement surface, the being positioned parallel to the distal end of the shaft; and
    at least one locking wing extending radially from the shaft, the at least one locking wing having a narrow end positioned about the first distance from the distal end and a wide end positioned at the proximal end, the locking wing tapering from the narrow end to the wide end being provided on one side of a first plane through the longitudinal axis of the suture anchor.

18. The suture anchor according to claim 17, wherein the engagement surface is configured to engage with an interface surface of the insertion tool.

19. The suture anchor according to claim 18, wherein the front part is cone shaped.

20. The suture anchor according to claim 17, wherein the proximal end of the shaft is acutely angled toward the distal end with respect to the longitudinal axis of the suture anchor.

21. The suture anchor according to claim 17, wherein the at least one locking wing includes a single locking wing extending radially from the shaft.

22. A toggling suture anchor for anchoring at least one suture thread to a bone, the toggling suture anchor being anchored by operation of an insertion tool, the suture anchor comprising:
   a shaft having
      a longitudinal axis,
      a distal end,
      a proximal end acutely angled toward the distal end with respect to the longitudinal axis of the suture anchor,
      at least one eyelet hole arranged starting at a first distance from the distal end off the longitudinal axis of the suture anchor to receive the suture thread,
      at least one suture groove extending parallel to the longitudinal axis of the shaft to provide a location to guide the suture thread while inserting the suture anchor into the bone,
      at least one stabilizing rib configured to contact an inner surface of a cylindrical distal end of the insertion tool to stabilize the suture anchor when coupled to the insertion tool;
   a cone-shaped front part extending from the distal end of the shaft and having an apex on the longitudinal axis and a base having an insertion tool engagement surface, the base being positioned parallel to the distal end of the shaft; and
   a single locking wing extending radially from the shaft, the single locking wing having a narrow end positioned about the first distance from the distal end and a wide end positioned at the proximal end, the locking wing tapering from the narrow end to the wide end being provided on one side of a first plane through the longitudinal axis of the suture anchor, said one side being opposite a side of the first plane through which the at least one eyelet hole extends perpendicularly.

23. An anchoring system for anchoring at least one suture thread to a bone, the anchoring system comprising:
   an insertion tool having a longitudinal tool axis; and
   a toggling suture anchor configured to be coupled to the insertion tool, the suture anchor including
   a shaft having a longitudinal axis, a distal end, a proximal end, at least one eyelet hole positioned starting at a first distance from the distal end to receive the suture, and at least one suture groove extending parallel to the longitudinal axis of the shaft to provide a location to guide the suture thread while inserting the suture anchor into the bone;
   a front part extending from the distal end of the shaft and having an apex on the longitudinal axis and a base having an insertion tool engagement surface, the base being positioned parallel to the distal end of the shaft; and
   at least one locking wing extending radially from the shaft, the at least one locking wing having a narrow end positioned about the first distance from the distal end and a wide end positioned at the proximal end, the locking wing tapering from the narrow end to the wide end being provided on one side of a first plane through the longitudinal axis, wherein during use of the insertion tool to insert the anchor in the bone, the longitudinal tool axis is parallel to the longitudinal axis of the suture anchor.

24. The anchoring system according to claim 23, wherein the at least one locking wing includes a single locking wing extending radially from the shaft.

25. The anchoring system according to claim 24, wherein the engagement surface is configured to engage with an interface surface of the insertion tool.

26. The anchoring system according to claim 25, wherein the front part is cone shaped.

* * * * *